US009023062B2

(12) United States Patent
Franklin et al.

(10) Patent No.: US 9,023,062 B2
(45) Date of Patent: May 5, 2015

(54) IMPLANTABLE ACCESS PORT DEVICE AND ATTACHMENT SYSTEM

(75) Inventors: Ethan Franklin, Goleta, CA (US); Janel A. Birk, Oxnard, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 833 days.

(21) Appl. No.: 12/426,057

(22) Filed: Apr. 17, 2009

(65) Prior Publication Data
US 2009/0264901 A1    Oct. 22, 2009

Related U.S. Application Data

(60) Provisional application No. 61/045,890, filed on Apr. 17, 2008.

(51) Int. Cl.
*A61B 17/12* (2006.01)
*A61M 39/04* (2006.01)
*A61M 39/02* (2006.01)
A61B 17/064 (2006.01)
A61B 17/068 (2006.01)
A61F 5/00 (2006.01)

(52) U.S. Cl.
CPC .......... *A61M 39/0208* (2013.01); *A61B 17/064* (2013.01); *A61B 17/068* (2013.01); *A61F 5/0056* (2013.01); *A61F 5/0089* (2013.01); *A61M 2039/0223* (2013.01)

(58) Field of Classification Search
USPC ............ 600/37, 184; 606/139, 140, 142, 157; 623/23.64, 23.65, 902, 23.72
See application file for complete search history.

(56) References Cited

U.S. PATENT DOCUMENTS

| 586,113 A | 7/1897 | Bott |
| 2,163,048 A | 6/1939 | McKee |
| 2,737,954 A | 3/1956 | Knapp |
| 3,371,352 A | 3/1968 | Siposs et al. |
| 3,569,660 A | 3/1971 | Houldcroft |

(Continued)

FOREIGN PATENT DOCUMENTS

| CN | 1250382 | 4/2000 |
| CN | 1367670 | 9/2002 |

(Continued)

OTHER PUBLICATIONS

Helioscopie Product Insert for Heliogast, pp. 1-11 (undated).

(Continued)

*Primary Examiner* — Ryan Severson
*Assistant Examiner* — Rachel S Papeika
(74) *Attorney, Agent, or Firm* — Gordon & Jacobson, PC

(57) ABSTRACT

A system for attaching an access port to bodily tissue includes an access port assembly and including an access port having a generally central axis. The access port assembly further includes an attachment mechanism structured to enable the access port to be attached, for example, to an abdominal muscle of a patient. The delivery tool includes a handle having a generally longitudinal axis and a delivery head structured to engage the access port assembly, and an activation mechanism for enabling deployment of the attachment mechanism when the delivery head is so engaged with the access port assembly. The delivery tool is configured such that the longitudinal axis of the handle is spaced apart from the generally central axis of the access port when the delivery head is so engaged with the access port assembly.

17 Claims, 6 Drawing Sheets

(56) References Cited

U.S. PATENT DOCUMENTS

| | | |
|---|---|---|
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,840,018 A | 10/1974 | Heifetz |
| 3,958,562 A | 5/1976 | Hakim et al. |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Showell et al. |
| 4,161,943 A | 7/1979 | Nogier |
| 4,164,943 A | 8/1979 | Hill et al. |
| 4,190,040 A | 2/1980 | Schulte |
| 4,233,992 A | 11/1980 | Bisping |
| 4,265,252 A | 5/1981 | Chubbuck et al. |
| 4,280,722 A | 7/1981 | Guptil et al. |
| 4,413,985 A | 11/1983 | Wellner |
| 4,474,572 A | 10/1984 | McNaughton et al. |
| 4,502,335 A | 3/1985 | Wamstad et al. |
| 4,543,088 A | 9/1985 | Bootman et al. |
| 4,557,722 A | 12/1985 | Harris |
| 4,569,675 A | 2/1986 | Prosl et al. |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A | 6/1987 | Fenton, Jr. et al. |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A * | 9/1988 | Wiita et al. .................. 604/175 |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A | 6/1989 | Hancock et al. |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A | 12/1989 | Johnston et al. |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,167,638 A | 12/1992 | Felix et al. |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,649,937 A * | 7/1997 | Bito et al. .................. 606/139 |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A | 12/1997 | Flaherty et al. |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,270,475 B1 | 8/2001 | Bestetti et al. |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |

(56) References Cited

U.S. PATENT DOCUMENTS

| | | |
|---|---|---|
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze et al. |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,530,943 B2 | 5/2009 | Lechner |
| 7,553,298 B2 | 6/2009 | Hunt et al. |
| 7,561,916 B2 | 7/2009 | Hunt et al. |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum et al. |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 | 10/2010 | Birk et al. |
| 7,850,660 B2 | 12/2010 | Uth et al. |
| 7,862,546 B2 | 1/2011 | Conlon et al. |
| 7,909,754 B2 | 3/2011 | Hassler, Jr. et al. |
| 7,909,804 B2 | 3/2011 | Stats |
| 8,007,474 B2 | 8/2011 | Uth et al. |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyer |
| 2002/0111621 A1* | 8/2002 | Wallace et al. ................ 606/41 |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0019315 A1 | 1/2004 | Blatter |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon |
| 2005/0131383 A1 | 6/2005 | Chen et al. |
| 2005/0148956 A1 | 7/2005 | Conlon |
| 2005/0149143 A1 | 7/2005 | Libbus et al. |
| 2005/0209573 A1 | 9/2005 | Brugger et al. |
| 2005/0240155 A1 | 10/2005 | Conlon |
| 2005/0240156 A1 | 10/2005 | Conlon |
| 2005/0267500 A1 | 12/2005 | Hassler, Jr. et al. |
| 2005/0277899 A1 | 12/2005 | Conlon |
| 2005/0283041 A1 | 12/2005 | Egle |
| 2005/0283118 A1* | 12/2005 | Uth et al. ................ 604/175 |
| 2005/0283119 A1 | 12/2005 | Uth et al. |
| 2006/0074439 A1 | 4/2006 | Garner et al. |
| 2006/0122578 A1 | 6/2006 | Lord et al. |
| 2006/0161186 A1 | 7/2006 | Hassler, Jr. et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1 | 9/2006 | Schulze |
| 2006/0235445 A1 | 10/2006 | Birk |
| 2006/0235448 A1 | 10/2006 | Roslin et al. |
| 2006/0247539 A1 | 11/2006 | Schugt et al. |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |

(56) References Cited

U.S. PATENT DOCUMENTS

| | | |
|---|---|---|
| 2007/0016231 A1 | 1/2007 | Jambor et al. |
| 2007/0027356 A1 | 2/2007 | Ortiz |
| 2007/0038255 A1 | 2/2007 | Kieval et al. |
| 2007/0060959 A1 | 3/2007 | Salo et al. |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon et al. |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe et al. |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 A1 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |

(56) References Cited

FOREIGN PATENT DOCUMENTS

| | | |
|---|---|---|
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 A1 | 12/2001 |
| WO | WO 02/10667 | 2/2002 |
| WO | 02074381 A2 | 9/2002 |
| WO | WO 02/074381 | 9/2002 |
| WO | WO 03/105732 | 12/2003 |
| WO | 2004019671 A2 | 3/2004 |
| WO | WO 2004/016971 | 3/2004 |
| WO | WO 2005/037055 A2 | 4/2005 |
| WO | WO 2005/072627 A1 | 8/2005 |
| WO | WO 2006/021695 | 3/2006 |
| WO | WO 2009/007526 | 1/2009 |
| WO | WO 2009/129474 | 10/2009 |

OTHER PUBLICATIONS http://en/wikipedia.org/Injection_Molding.
Autumn K. et al.; "Evidence of Van Der Waals Adhesion in Gecko Setae"; PNAS; vol. 99; No. 19; pp. 12252-12256; Sep. 17, 2012.
Geim AK. et al.; "Microfabricated Adhesive Mimicking Gecko Foot-Hair"; Nature Materials Abstract only; vol. 2; No. 7; 2003.
Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.
Yurdumakan B., et al.; "Synthetic Gecko Foot-Hairs from Multiwalled Carbon Nanotubes"; The Royal Society of Chemistry; p. 3799-3801; 2005.

* cited by examiner

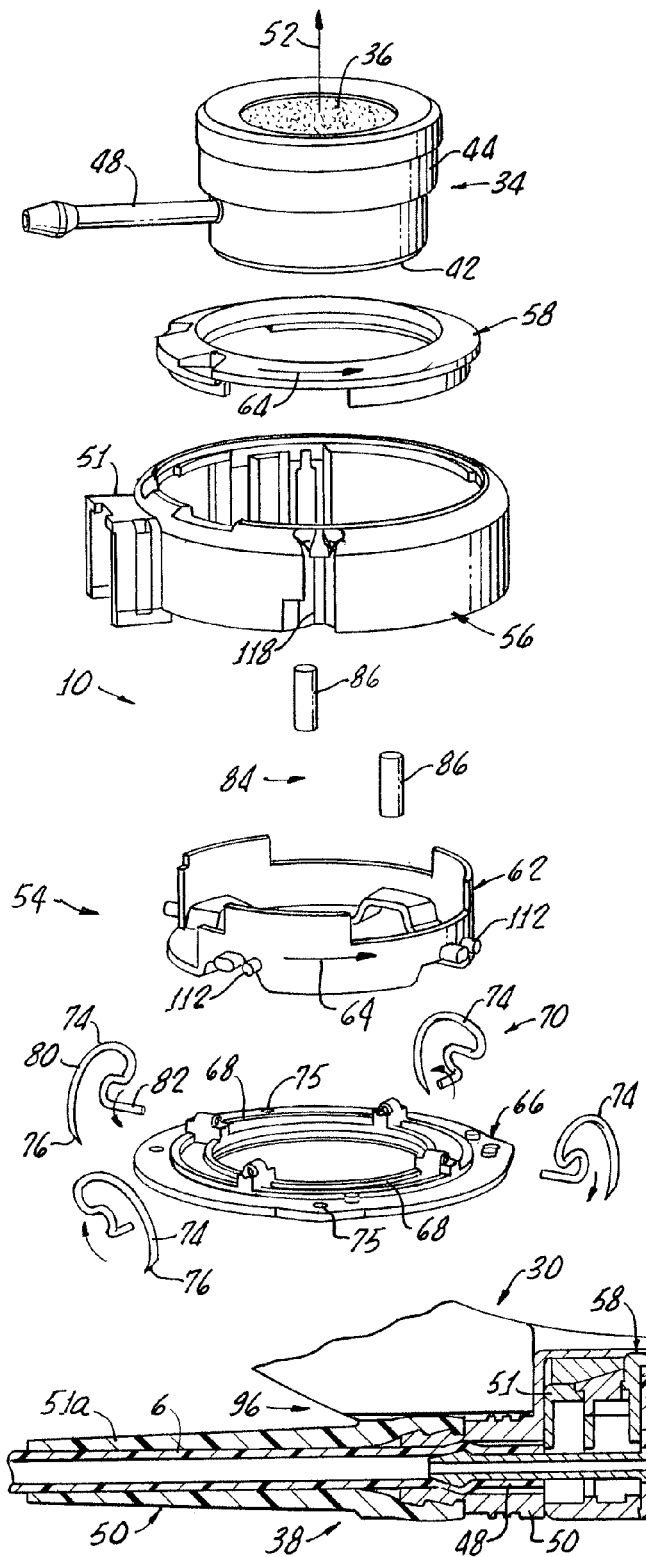

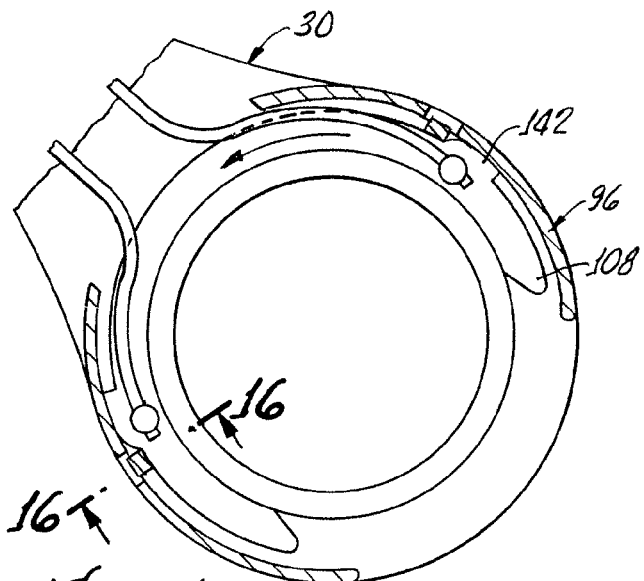
FIG. 14.
FIG. 13.
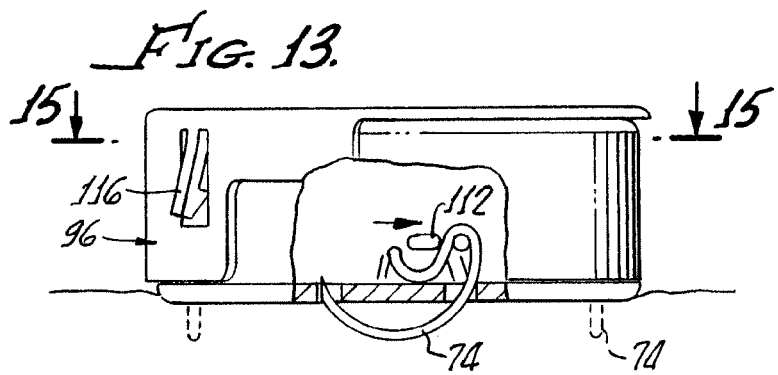
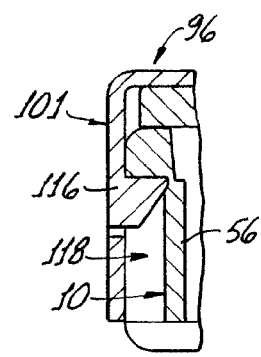
FIG. 16.
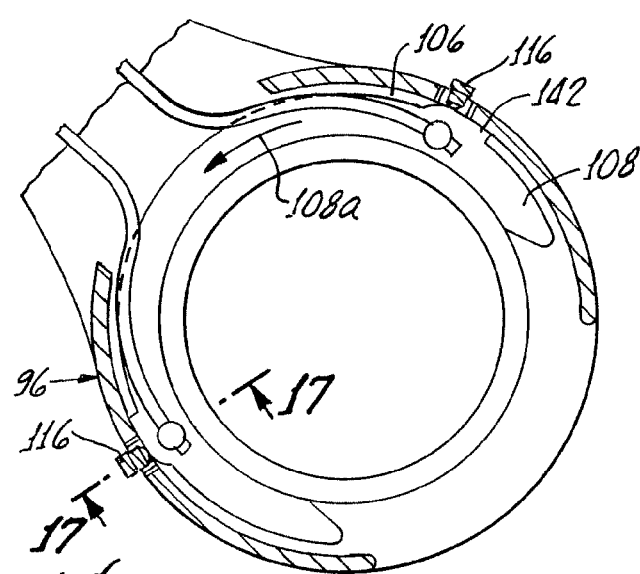
FIG. 15.
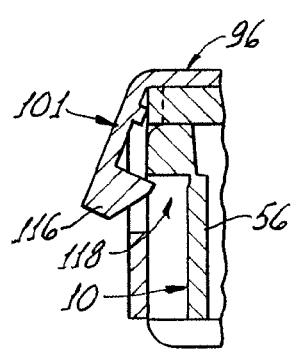
FIG. 17.

IMPLANTABLE ACCESS PORT DEVICE AND ATTACHMENT SYSTEM

RELATED APPLICATIONS

This application claims the benefit of U.S. Provisional Patent Application No. 61/045,890 filed on Apr. 17, 2008, the entire disclosure of which is incorporated herein by this specific reference.

BACKGROUND

The present invention generally relates to medical implants and more specifically relates to an implantable access port device and an attachment mechanism for attaching such an access port device to tissue.

Medical implants for performing therapeutic functions for a patient are well known. Such devices include pace makers, vascular access ports, injection ports (such as used with gastric banding systems) and gastric pacing devices. Such implants need to be attached, typically subcutaneously, in an appropriate place in order to function properly. It is desirable that the procedure to implant such devices be quick, easy and efficient and require as small of an incision as possible.

SUMMARY OF THE INVENTION

The present invention is directed to a system including an implantable access port, for example, but not limited to, an implantable access port for use in inflating and deflating an inflatable a gastric band. Generally, the system includes an access port configured to be connected, for example, by means of a fluid conduit, to an inflatable portion of a gastric band. Access ports for use with gastric bands are well known and are described, for example, in U.S. patent application Ser. No. 10/562,964 filed on Sep. 15, 2004; U.S. patent application Ser. No. 10/562,954 filed on Jan. 21, 2005; Ser. No. 11/472,902 filed on Jun. 22, 2006; U.S. patent application Ser. No. 11/444,702, filed on May 31, 2006 and U.S. patent application Ser. No. 11/540,177, filed on Sep. 29, 2006, the entire disclosure of each of these patent applications being incorporated herein by this specific reference.

In one aspect of the invention, a system for attaching an access port to bodily tissue is provided.

The system generally comprises an access port assembly including an access port and an access port housing generally containing the access port. The access port may be structured for holding, receiving and enabling passage of a fluid between the access port assembly and a patient or into another implanted device in a patient, for example, a gastric band.

For example, the access port includes a bottom, a sidewall and a needle penetratable septum. The needle penetratable septum is spaced apart from the bottom and lies in a plane approximately parallel therewith. The sidewall, bottom and septum define a space for holding fluid. The access port assembly has a generally central axis extending through the bottom, the septum and the space for holding fluid. The sidewall generally surrounds this axis and is radially spaced therefrom.

The access port assembly further includes an attachment mechanism, including, for example, a plurality of rotatable anchors having a deployed position and an undeployed position. When in the deployed position, the anchors fix the access port to bodily tissue. In the case where the system is used in conjunction with a gastric band, the access port assembly may be secured, by means of the anchors, to the rectus muscle fascia.

In some embodiments, the attachment mechanism is reversible, allowing the implantable medical device to be detached from tissue.

In a specific embodiment, each of the anchors is made of wire, for example, a bent, stainless steel wire having round cross section and a multi-faceted, sharp distal tip.

In one embodiment, the plurality of anchors comprises four anchors spaced apart about the access port. Each anchor includes a curved distal portion which engages tissue and a pivotal proximal portion which is rotatably connected to the access port housing. In some embodiments, the pivotal proximal portion is substantially perpendicular with the curved distal portion, or more specifically, substantially perpendicular with a plane in which the curved distal portion rotates when the anchors are moved into the deployed position. In some embodiments, each anchor may include a generally spiral distal portion and a straight proximal portion substantially perpendicular with the spiral distal portion. A cam system may be used as a means for actuating deployment of the anchors, for example, upon rotation of a rotating activator of the access port housing.

In another aspect of the invention, the system further comprises a delivery tool structured to facilitate attachment of the access port assembly to bodily tissue. The tool includes a handle having a generally longitudinal axis and a distal portion structured to couple with or engage the access port assembly. The tool further includes an activation mechanism for activating deployment of the attachment mechanism. In some embodiments, the tool is configured such that the generally longitudinal axis of the handle is spaced apart from the generally central axis of the access port when the delivery tool is so engaged with the access port assembly. For example, the delivery head of the tool is offset from the tool handle. For example, the tool has a generally, non-linear, or curved, configuration with the delivery head being located forward of, or extending away from, the handle.

In another aspect of the invention, the activation mechanism of the tool comprises a cable mechanism, for example, two cables extending from a proximal end of the tool along the tool handle to the delivery head. In a specific embodiment, the cable mechanism comprises two opposingly movable cables. Longitudinal displacement of the cable mechanism causes rotational movement of the anchors when the tool is engaged to the access port assembly. The cables may be made of tungsten, or a tungsten material. Generally, each cable includes a substantially straight proximal portion extending along the handle of the tool and a curved distal portion connected to a rotating element of the delivery head.

Each and every feature described herein, and each and every combination of two or more of such features, is included within the scope of the present invention provided that the features included in such a combination are not mutually inconsistent.

BRIEF DESCRIPTION OF THE DRAWINGS

The invention may be better understood with reference to the following Detailed Description and Drawings of which:

FIG. 6 is an exploded view of the access port assembly shown in FIG. 5;

FIG. 6A is a cross-sectional view of the access port assembly coupled with the delivery head;

FIG. 7 is a partial cross-sectional side view of the system shown in FIG. 4;

FIGS. 8A and 8B are cross-sectional side views of the proximal portion of the tool showing an activation mechanism in an unlocked state and a locked state, respectively;

FIGS. 11, 12 and 13 show a cut-away view of the access port with an anchor thereof in an undeployed state, a partially deployed state and a fully deployed state, respectively;

FIG. 14 shows a cross-sectional view of a top of the tool taken along line 14-14 of FIG. 12;

FIG. 15 is a cross-sectional view taken along lines 15-15 of FIG. 13;

FIG. 16 is a cross-sectional view taken along lines 16-16 of FIG. 14; and

FIG. 17 is a cross-sectional view taken along lines 17-17 of FIG. 15.

DETAILED DESCRIPTION

Figure 1:
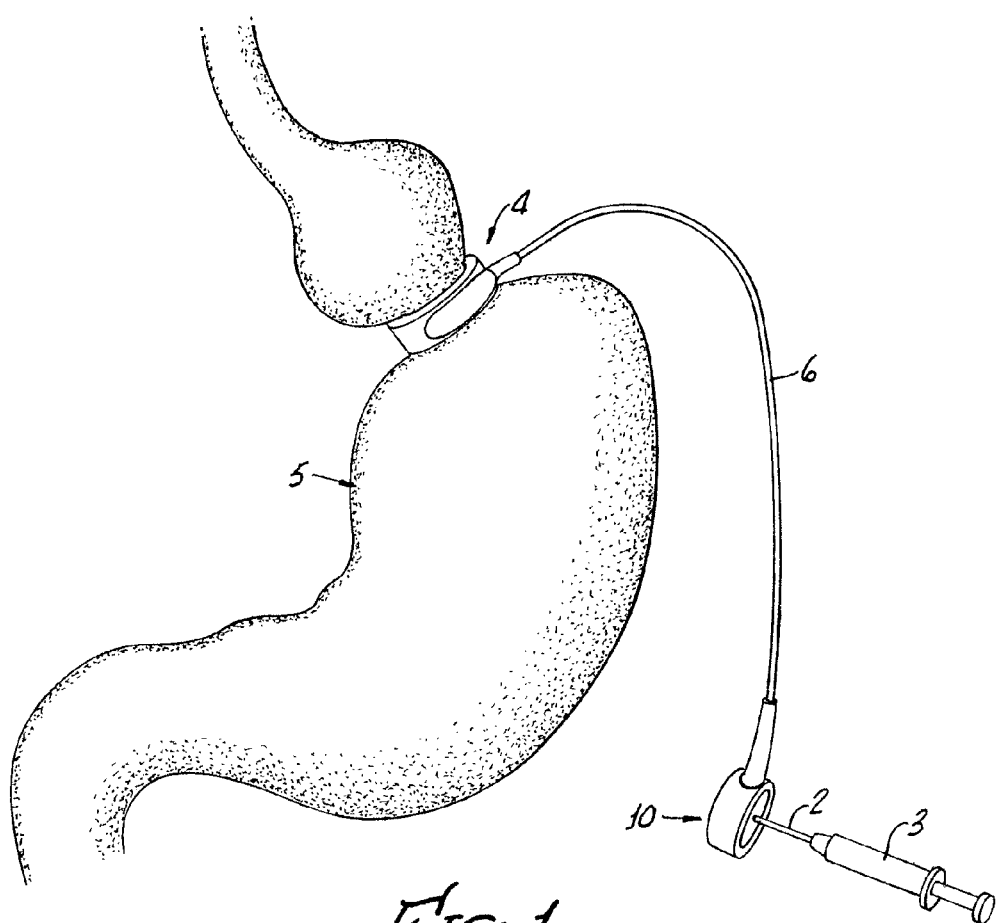
FIG. 1 is a simplified perspective view of an access port assembly of a system of the invention as implanted in a patient and being used for inflation and deflation of a conventional gastric band for treating obesity.
Figure 2:
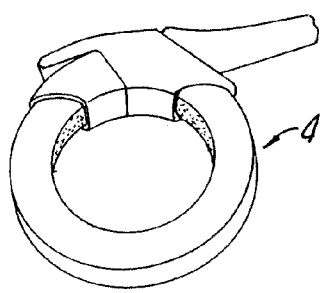
FIGS. 2 and 3 are perspective views of a conventional gastric band useful in conjunction with the system of the present invention, the gastric band being shown in a deflated state and an inflated state, respectively.
Figure 3:
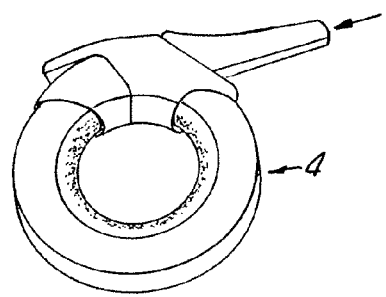

Turning now to FIG. 1, a simplified perspective view of an access port assembly 10 of a system of the invention is shown. The access port assembly 10 is shown as it is being penetrated by a needle 2 of a manually operable syringe 3. By passing fluid into the access port assembly 10, or removing fluid by means of the access port assembly 10, as will be described in greater detail hereinafter, the needle 2 and syringe 3 provide a convenient means for inflating and/or deflating a conventional gastric band 4, thereby enabling adjustment of a size of a stoma or a level of restriction on a patient's stomach 5. The gastric band 3 is shown in a deflated state in FIG. 2 and an inflated state in FIG. 3, and is not considered, in itself, to make up an embodiment of the present invention.

Figure 4:
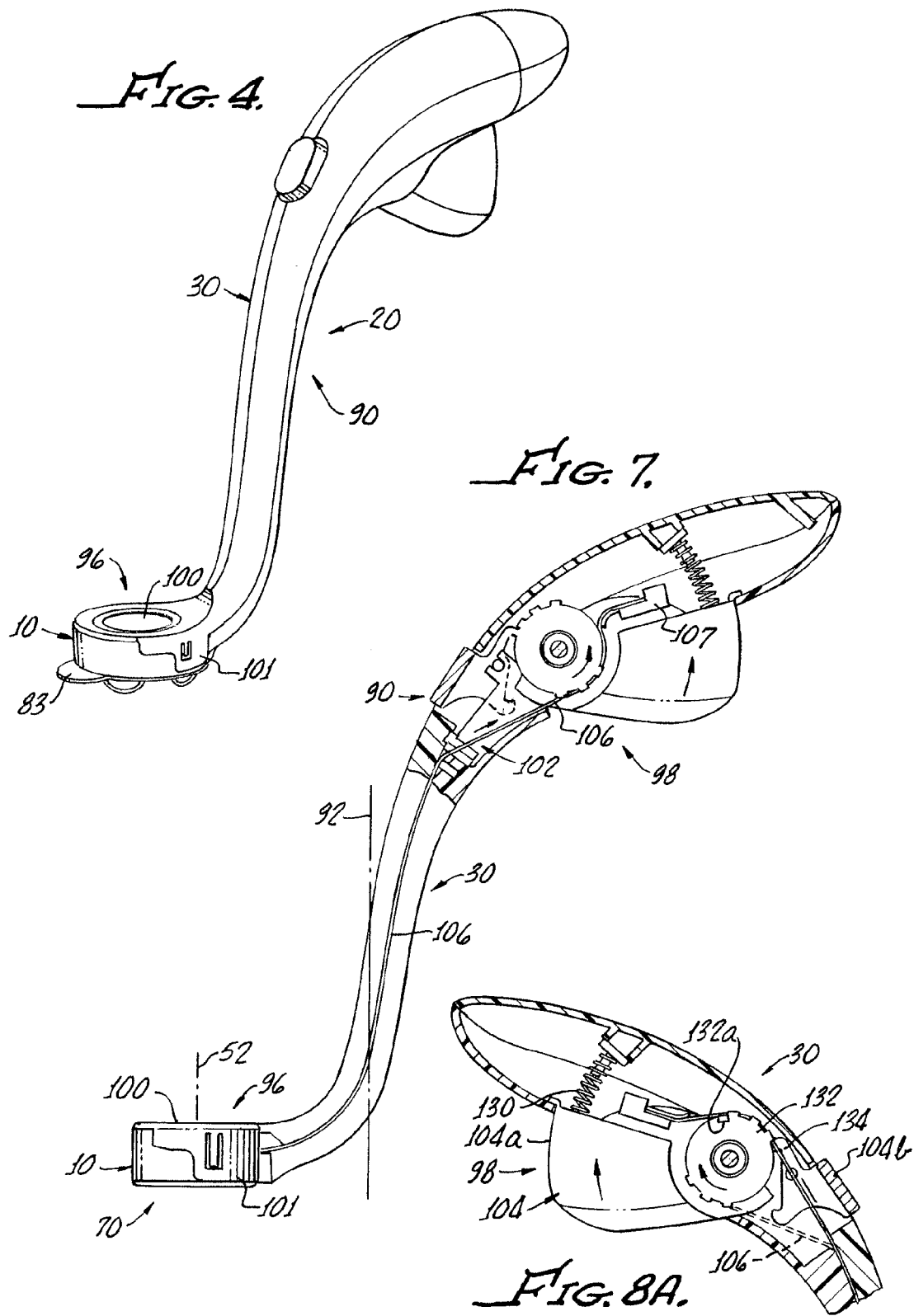
FIG. 4 is a perspective view of a system in accordance with the present invention, including an access port assembly and a delivery tool for applying the access port assembly to bodily tissue.

Turning now to FIG. 4, a system 20 in accordance with one embodiment of the invention is shown. The system 20 generally includes an implantable access port assembly 10 and a tool 30 for fixing the access port assembly 10 to bodily tissue. The access port assembly 10 is configured to be connected, for example, by means of a fluid line 6 (see FIG. 1) to an inflatable portion of a gastric band 4.

Figure 5:
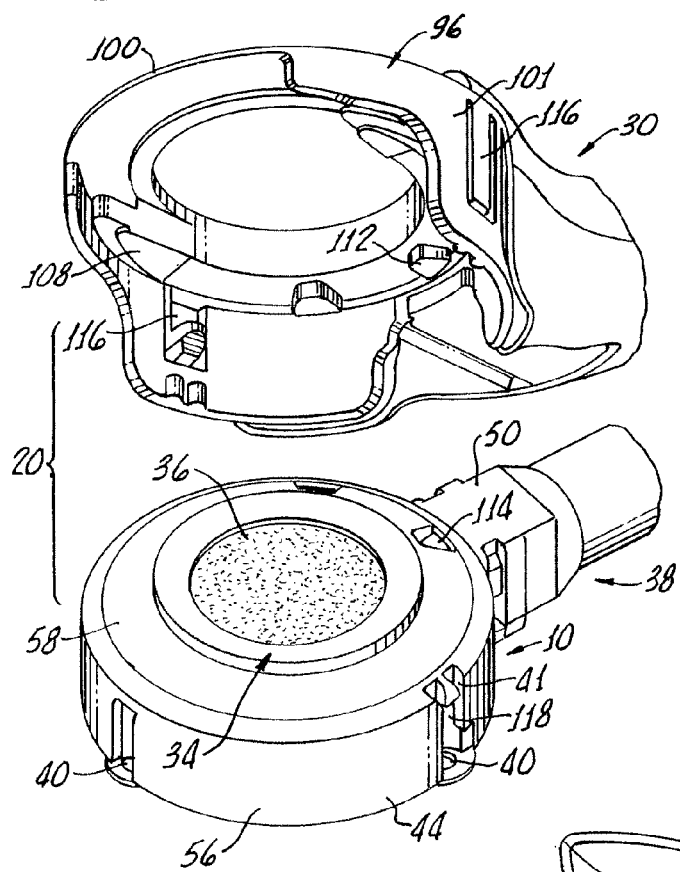
FIG. 5 is a perspective view of the access port assembly and a delivery head of the tool separated from the access port assembly, of the system shown in FIG. 4.

Referring now to FIG. 5, the access port assembly 10 generally comprises an access port 34 having a septum 36, a chamber 37 (shown in FIG. 6A) and an inlet/outlet connector 38 in communication with the chamber 37. The access port 34 is structured for holding, receiving and enabling passage of a fluid between inlet/outlet connector 38 and fluid line 6.

In the shown embodiment, the access port assembly 10 includes accommodations for facilitating suturing thereof to the patient, in the event that the use of the tool 30 to attach the access port assembly 10 is not desired. For example, suturing holes 40 are provided. Needle clearance regions 41 may also be provided to facilitate suturing.

The access port assembly 10 is shown in detail in FIGS. 6 and 6A. The access port 34 includes an access port bottom 42, a substantially cylindrical access port sidewall 44 and needle penetratable septum 36. The access port 34 further includes passage for example, outlet barb 48, extending from chamber 37, which makes up a part of an inlet/outlet connector 38 coupleable to fluid line 6.

Inlet/outlet connector 38 may comprise a strain relief element 50 which locks into a coupler 51 of housing sidewall 56 and protects fluid line 6 from folding, kinking, rotating or torquing where line 6 connects to the access port assembly 10. Further strain relief may be provided by flexible sleeve 51a. Flexible sleeve 51a may be made of a puncture-resistant material, and, along with strain relief element 50, provides protection against accidental needle puncture to line 6.

The septum 36 is spaced apart from the access port bottom 42 and lies in a plane approximately parallel therewith. Septum 36 may be made of any suitable needle penetratable material, for example—a self sealing, needle penetratable material. The access port sidewall 44, access port bottom 42 and septum 36 define a chamber 37, or space, for holding fluid. The access port bottom 42 and access port sidewall 44 may be integral components of a substantially unitary structure made of a biocompatible metallic material, for example, titanium. Outlet barb 48 may also be made of the same material.

The access port assembly 10 has a generally central axis, indicated by line 52 in FIG. 6, extending through the access port bottom 42, the septum 36 and the chamber 37. The access port sidewall 44 generally surrounds the generally central axis 52 and is radially spaced apart therefrom. It should be appreciated that when the access port assembly 10 is implanted for use in a patient, the generally central axis 52 is generally perpendicular to the surface of the tissue or muscle to which the access port assembly is attached.

The access port assembly 10 further includes a housing 54 including a housing sidewall 56 substantially surrounding the access port sidewall 44, and an actuator assembly. Actuator assembly is made up of an actuator cap 58 and actuator element 62 which are rotatable (as indicated by arrows 64 on actuator cap and actuator element 62) with respect to the housing sidewall 56. The housing 54 further includes an anchor base 66 including tracks 68 for receiving actuator element 62.

The access port assembly 10 further includes an attachment mechanism 70. The attachment mechanism 70 is structured to anchor or fix the access port assembly 10 to the patient. The attachment mechanism 70 may comprise, for example, a plurality of rotatable anchors 74 which are movable between an undeployed position and a deployed position.

In the shown embodiment, the plurality of rotatable anchors 74 comprises four anchors 74. The anchors 74 are generally spaced apart for example, substantially equidistantly spaced apart, about a circumference of the access port 34. When in the undeployed position, the anchors 74 are substantially concealed and contained between the actuator element 62 and the housing sidewall 56. During deployment, the anchors 74 rotate and travel out of their contained, substantially concealed position to an exposed position, by sliding through apertures 75 in anchor base 66.

Each anchor 74 may be made of a wire, for example, stainless steel wire. The anchor 74 may comprise a bent wire having a generally round cross-section and a sharp distal tip 76.

The anchor tip 76 is structured to penetrate and enter bodily tissue as the anchor 74 rotates into the deployed position. In some embodiments, the anchor tip 76 includes one or more flat faces. For example, the tip 76 may have a single facet, or may be multi-faceted. For example, the tip 76 may have two facets or three or more facets.

In a specific embodiment, the anchors 74 are a bent stainless steel wire have a generally arc shape having an arc diameter of slightly less than about 0.5 inch and a constant circular cross section of about 0.023 inch diameter.

Each anchor 74 includes a curved distal portion 80 which engages tissue and a pivotal proximal portion 82 which is rotatably connected to the anchor base 66 of the port housing. In the shown embodiment, the pivotal proximal portion 82 is substantially perpendicular with the curved or spiral distal portion 80, or more specifically, substantially perpendicular with a plane in which the curved distal portion moves when the anchors 74 are rotated into the deployed position.

Turning briefly to FIG. 4, the access port assembly 10 may further comprise a removable safety cap 83 to protect a physician's or medical personnel's hands and fingers from accidental anchor sticks. The safety cap 83 mounts to the bottom of the access port housing 54 by a press-on fit. The color of the safety cap 83 may be an easily distinguishable from the port housing color.

Referring back now to FIG. 6, the access port assembly 10 may include one or more locator elements 84, for example, at least one or two or more radio opaque markers 86 that are clearly visible under an x-ray. These may be secured in port housing 54 and spaced apart from the access port 34 so as not to hide the marker image with an image of the access port 34. In a specific embodiment, two markers 86 are provided, each having dimensions of about Ø0.075"×0.200" in length a separation distance from the access port 34 of at least about 0.100" in. The markers can be used to facilitate identification of the type of gastric band or other useful information to be identified by an X-ray image of the access port assembly 10, for example, by using varied configurations of markers 86.

As shown in FIG. 7, the tool 30 includes a handle 90 having a generally longitudinal axis (indicated by line 92) and a distal portion 96 structured to be removably and functionally coupled to the access port assembly 10.

In the shown embodiment, the tool 30 is configured such that the generally longitudinal axis of the handle 90 is spaced apart from, or not aligned with, the generally central axis 52 of the access port 34 when the tool 30 is coupled with the access port assembly 10. In other words, the delivery head 96 of the tool 30 which engages the access port assembly 10 is offset from the tool handle 90, i.e., the portion of the tool 30 that is handled by an operator thereof. In some embodiments, the generally central axis of the access port 34 and the longitudinal axis of the handle are offset a distance of at least about one inch to about two inches or more.

For example, the tool 30 has a generally curved, scoop shaped, L-shaped, or similar "offset" configuration such that the delivery head 96 is located forward with respect to, or extending away from, the handle 90. This configuration enables the tool 30 to be used to implant the access port assembly 10 using a relatively small incision for example, in comparison to a conventional applier or tool that is substantially unilinear in configuration, or requires the tool to be substantially entirely aligned with a central axis of a similarly sized access port during surgical implantation. During implantation of the access port assembly 10, a physician inserts the delivery head 96 into an incision that is somewhat offset from the implantation site, that is, the target location where the access port is attached.

Figure 8B:
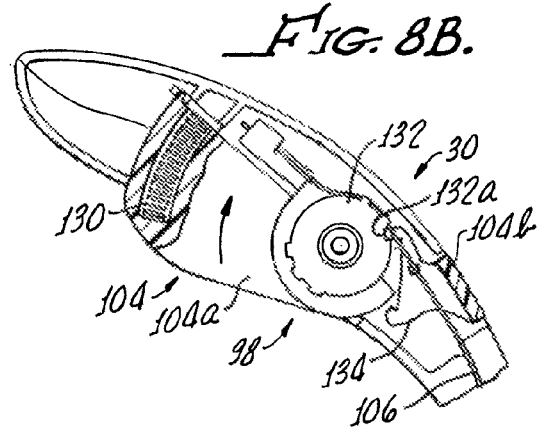

Turning now as well to FIGS. 8A and 8B, the tool 30 includes an activation mechanism 98. Activation mechanism 98 enables automatic deployment of the attachment mechanism 70, for example, by a physician using the system 10 to attach the access port assembly 10 to a patient. Activation mechanism 98 will be described in greater detail elsewhere herein.

Figure 9:
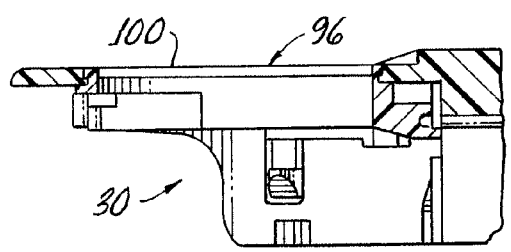
FIG. 9 is a side view of the distal portion of the tool.

FIG. 9 shows a side view of the delivery head 96 of the tool 30. Delivery head 96 includes top 100 and sidewall 101. When tool 30 is coupled with access port assembly 10, top 100 extends over at least a portion of access port 34 and actuator cap 58 (see FIG. 5) and sidewall 101 extends around and clips to at least a portion of housing sidewall 56.

Turning back to FIGS. 8A and 8B, in this exemplary embodiment, the activation mechanism 98 comprises a cable mechanism 102 coupled to a trigger mechanism 104.

The cable mechanism 102 comprises two opposingly movable cables 106 made of tungsten or similar material. The cables 106 extend from the trigger mechanism 104 along the tool handle 90 to the delivery head 96 of the tool 30. Trigger mechanism 104 includes a manually compressible trigger 104a and a trigger release button 104b.

Generally, each cable 106 includes a substantially straight proximal portion extending along the handle of the tool 30 and a curved distal portion connected to the rotating element 108 of the delivery head 96 (see FIG. 5). Suitable structure, for example, cable anchor 107 is provided to secure cables 106 in place. Cables 106 are movable in mutually opposing directions upon rotation of wheel 132.

In order to deploy staples 74, an operator presses trigger 104a as indicated in FIG. 8A. Compression of trigger 104 causes compression of spring 130, rotation of wheel 132 and longitudinal displacement of cable 106. Trigger latch 134 is biased against wheel 132, for example by means of a spring (not shown). Once trigger 104a is fully compressed as shown in FIG. 8B, trigger latch 134 engages wheel 132 at detent notch 132a (detent notch 132 may be more clearly seen in FIG. 8A) and locks trigger mechanism 104. When trigger 104a is fully compressed, trigger release button 104b is "out" as shown in FIG. 8B. In order to cause anchors 74 to retract, an operator presses trigger release button 104b, which disengages trigger latch 134 from detent notch 132a and load on spring 130 causes reverse rotation of the wheel 132.

Turning as well, briefly to FIGS. 5 and 6, longitudinal displacement of cable 106, activated by manually pressing trigger 104a, causes rotation of rotating element 108 and reciprocal rotation of actuator cap 58. Rotation of actuator cap 58 causes reciprocal rotation of actuator element 62 and deployment of anchors 74.

Rotation of actuator element 62 causes rotation of each anchor 74.

Figure 11:
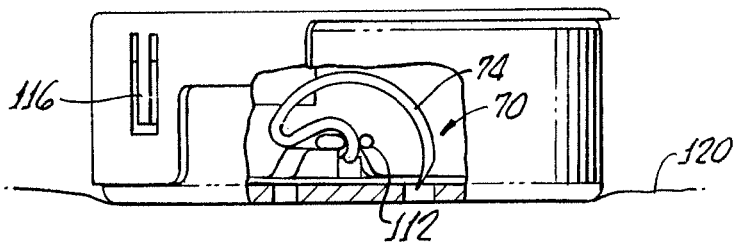
Figure 12:
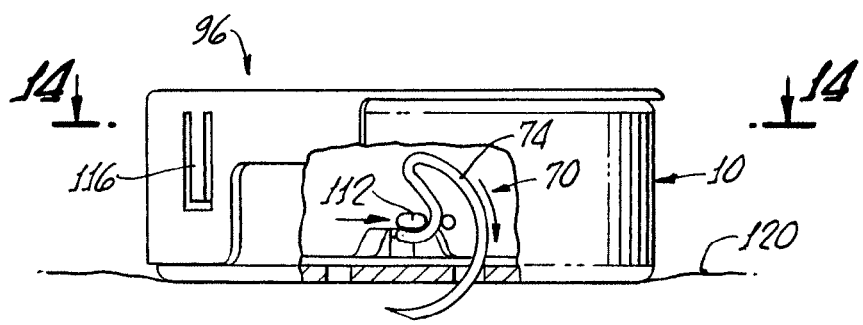

FIGS. 11, 12 and 13 illustrate deployment of an anchor 74 from a retracted, undeployed, position, through a rotating, deploying, position, to an actuated position, respectively.

Figure 10:
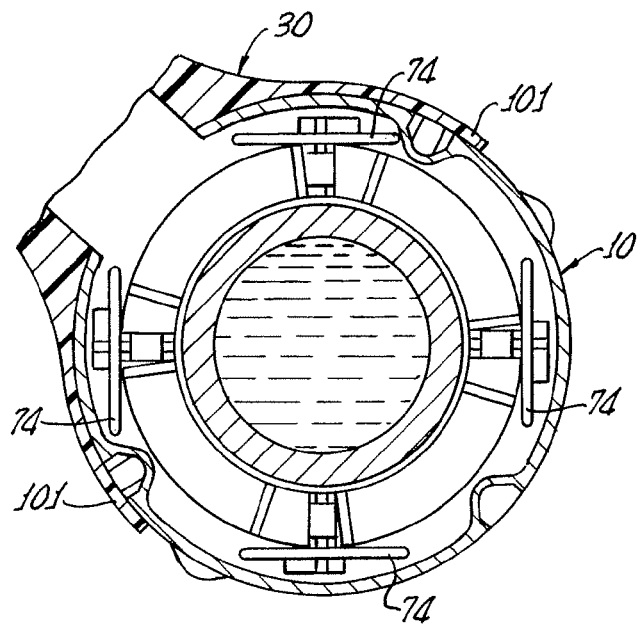
FIG. 10 is a cross-sectional view of the distal portion of the tool and the access port assembly of the system of the invention.

Referring now to FIGS. 5 and 10, the distal portion of tool 30 is coupled to access port assembly 10 by inserting access port assembly 10 between sidewall 101 of distal portion 30. When tool 30 is engaged to access port assembly 10, protrusions 112 of rotating element 108 are fixed in receiving ports 114 of actuator cap 58 and clips 116 of distal portion sidewall 101 engage undercuts 118 of housing sidewall 56.

Turning briefly to FIGS. 11, 12 and 13, access port assembly 10 is shown in partial cross-sectional view, as it is being stapled or fixed to an abdominal muscle fascia 120.

FIGS. 11-17 show different views of the access port assembly 10 and delivery head 96 during anchor deployment.

More particularly, FIG. 11 shows attachment mechanism 70 prior to deployment of anchor 74.

FIGS. 12, 14 and 16 show delivery head 96 and access port assembly 10 during deployment of anchor 74. As shown in FIG. 16, during deployment and prior to full deployment, clip 116 of delivery head 96 secures to undercut 118 of housing sidewall 56.

As shown in FIGS. 13, 15, and 17, when the activation mechanism 98 is fully deployed, structure, for example, berm 142 of rotating element 108, forces clip 116 outward and out of engagement with undercut 118, thereby decoupling access port assembly 10 from delivery heard 96.

Example

Use of the System

The following example describes one manner of using the presently shown and described system 20 of the invention to attach the access port assembly 10 to a gastric banding patient.

Referring generally to the Figures, the physician threads the strain relief element 50 over soft tubing 6 leaving about 2 cm of the tubing extending beyond locking end of strain relief element 50.

The tubing is then coupled to barb 48 until flush with housing sidewall 56 of port housing 54. The strain relief element 50 is then pushed into and locked onto coupler 51.

The physician checks that the trigger mechanism 104 is in a fully opened position such as shown in FIG. 7.

The physician inserts the access port assembly 10 into the delivery head 96 of the tool 30 by placing the access port assembly 10 on a table with the safety cap 83 in contact with the table (FIG. 4), and pressing delivery head 96 against access port assembly 10 in a direction along axis 52 of FIG. 7. This causes the access port assembly 10 to snap into delivery head 96. The safety cap 83 is then manually removed from the access port assembly 10. At this point, the anchors 74 are positioned as shown in FIG. 11.

The physician places tubing from the gastric band into the abdomen. The access port assembly 10 is placed lateral to a trocar opening and a pocket is created for the access port assembly 10 so that it is placed far enough from the trocar path to avoid abrupt kinking of the tubing. The tubing path is placed such that that the tubing will form a straight line with a gentle arching transition into the abdomen. The tubing is placed perpendicular to the midline of the patient.

The physician verifies that the fat has been fully cleared and the rectus muscle fascia is visible. The delivery head 96 of the tool 30 with access port assembly 10 coupled thereto is placed into a dissected pocket in an angled position to facilitate insertion. The access port assembly 10 is place flat against the fascia to ensure that all anchors 74 will fully engage the fascia and/or muscle tissue. The physician applies finger pressure to the top 100 of delivery head 96 to insure the access port assembly 10 is flat against the fascia and the tool 30 is steadied for firing.

The physician firmly squeezes the trigger mechanism 104 until it is fully closed thereby deploying the anchors 74 into the underlying fascia. At this point, the activation mechanism 98 is locked in a closed position as shown in FIG. 8B and the anchors 74 are fully deployed as shown in FIGS. 13, 15 and 17.

In order to disengage the tool 30 from the access port assembly 10, the physician slides the delivery head 96 away from the access port assembly 10 for example, horizontally or laterally, and lifts the tool 30 out of the incisional site. The physician ensures that the anchors 74 are fully engaged into fascia by running a finger around the base of the access port assembly.

In the event the access port assembly 10 is to be disengaged from the facia and repositioned, the trigger release button is pressed which unlocks the latch mechanism from the position shown in FIG. 8B which releases the trigger mechanism 104. Once the trigger is fully open the stainless steel anchors will be completed retracted back into the access port assembly 10. The access port assembly 10 can then be redeployed using tool 30 as described hereinabove, in a different, for example, more desirable location.

Numerous benefits have been described which result from employing the concepts of the present invention. The foregoing description of one or more embodiments of the invention has been presented for purposes of illustration and description. It is not intended to be exhaustive or to limit the invention to the precise form disclosed. Modifications or variations are possible in light of the above teachings and are considered to be within the scope of the invention. The one or more embodiments were chosen and described in order to illustrate the principles of the invention and its practical application to thereby enable one of ordinary skill in the art to utilize the invention in various embodiments and with various modifications as are suited to the particular use contemplated.

What is claimed is:

1. A system for attaching an access port to bodily tissue, the system comprising:
   an access port assembly including:
      i. an access port having a generally central axis and including a bottom, a sidewall and a needle penetrable septum; and
      ii. an attachment mechanism structured to enable the access port to be attached to bodily tissue; and
   a delivery tool including:
      i. a delivery head structured to engage the access port assembly, the delivery head having a longitudinal sidewall extending parallel to the central axis when the delivery head engages the access port;
      ii. a handle having a distal portion extending laterally away from the longitudinal sidewall of the delivery head and having a moveable trigger extending from a proximal portion of the handle, the handle defining an internal pathway in which a pair of opposingly moveable cable portions extend side-by-side, the cable portions extending from the delivery head into the internal pathway of the handle, the cable portions being oppositely longitudinally moveable side-by-side relative to each other in the internal pathway and in the delivery head by movement of the trigger; and
      iii. an activation mechanism coupled to the trigger for selectively enabling deployment and retraction of the attachment mechanism by movement of the trigger and a respective one of the cable portions when the delivery head is so engaged with the access port assembly.

2. The system of claim 1 wherein the handle extends away from the delivery head in a direction that does not intersect the generally central axis when the delivery head is so engaged with the access port assembly.

3. The system of claim 2 wherein the access port bottom is integral with the access port sidewall and the access port sidewall and access port bottom are a unitary configuration.

4. The system of claim 3 wherein the access port sidewall and access port bottom are titanium.

5. The system of claim 3 wherein the access port assembly further includes a housing including a housing sidewall surrounding the access port sidewall and an actuator assembly rotatable with respect to the housing sidewall.

6. The system of claim 1 wherein at least one of the cable portions includes tungsten.

7. The system of claim 1 wherein displacement of a respective one of the cable portions causes rotational movement of the attachment mechanism when the delivery head is engaged to the access port assembly.

8. The system of claim 1 wherein each of the cable portions has a substantially straight proximal portion and a curved distal portion.

9. The system of claim 1 wherein the attachment mechanism comprises at least one wire anchor.

10. The system of claim 9 wherein the wire anchor comprises a bent wire having a multi-faceted tip.

11. The system of claim 1 wherein the attachment mechanism comprises at least one anchor having a curved distal portion and a pivotal proximal portion substantially perpendicular with the curved distal portion.

12. The system of claim 1 wherein the attachment mechanism comprises at least one anchor having a spiral distal portion and a straight proximal portion substantially perpendicular with the spiral distal portion.

13. The tool of claim 1 wherein each of the cable portions has a substantially straight proximal portion and a curved distal portion.

14. The system of claim 1 wherein the delivery head has a substantially flat top surface and a substantially curved side surface, further wherein the handle is attached to the curved side surface of the delivery head.

15. A delivery tool for attaching an access port assembly to bodily tissue, the access port assembly including deployable fasteners and an access port having a generally central axis, the tool comprising:

a delivery head structured to engage the access port assembly, the delivery head having a longitudinal sidewall extending parallel to the central axis when the delivery head engages the access port;

a handle having a distal portion extending laterally away from the longitudinal sidewall of the delivery head and having a moveable trigger extending from a proximal portion of the handle, the handle defining an internal curved pathway in which a pair of opposingly movable cable portions extend side-by-side, the cable portions extending from the delivery head into the internal pathway of the handle, the cable portions being oppositely longitudinally displaceable side-by-side relative to each other by movement of the trigger; and an activation mechanism coupled to the trigger for selectively enabling deployment and retraction of the deployable fasteners by movement of the trigger and a respective one of the cable portions when the delivery head is so engaged with the access port assembly, wherein movement of the trigger is constructed to longitudinally displace a respective one of the cable portions in the internal pathway of the handle and in the delivery head to rotate a rotatable portion of the access port assembly when the delivery head is engaged to the access port assembly to move the deployable fasteners relative to the access port assembly, and wherein each of the cable portions has a substantially straight proximal portion and a curved distal portion.

16. The tool of claim 15 wherein at least one of the cable portions includes tungsten.

17. The tool of claim 15 wherein the delivery head has a substantially flat top surface and a substantially curved side surface, further wherein the handle is attached to the curved side surface of the delivery head.

* * * * *